US006660504B2

(12) United States Patent
Yamane et al.

(10) Patent No.: US 6,660,504 B2
(45) Date of Patent: Dec. 9, 2003

(54) PROCESS FOR EXCHANGING BASES IN PHOSPHOLIPIDS

(75) Inventors: Tsuneo Yamane, Nagoya (JP); Yugo Iwasaki, Chita (JP); Yukiko Mizumoto, Nishikasugai-gun (JP); Masaaki Kasai, Tokyo-to (JP); Takahiro Okada, Nagoya (JP)

(73) Assignee: Rinoru Oil Mills Co., Ltd., Tokyo (JP)

( * ) Notice: Subject to any disclaimer, the term of this patent is extended or adjusted under 35 U.S.C. 154(b) by 0 days.

(21) Appl. No.: 10/042,280

(22) Filed: Jan. 11, 2002

(65) Prior Publication Data

US 2002/0106744 A1 Aug. 8, 2002

(30) Foreign Application Priority Data

Jan. 11, 2001 (JP) ........................................ 2001-003382
Sep. 28, 2001 (JP) ........................................ 2001-301656

(51) Int. Cl.$^7$ .............................. C12N 9/16; C12P 9/00; C12P 7/64; C12P 13/04
(52) U.S. Cl. .................... 435/106; 435/117; 435/131; 435/176; 435/177; 435/180; 435/194
(58) Field of Search ................................ 435/117, 194, 435/131, 177, 176, 180, 106

(56) References Cited

U.S. PATENT DOCUMENTS 5,445,955 A * 8/1995 Ikuta et al. ................. 435/180

FOREIGN PATENT DOCUMENTS

| EP | 0 776 976 A2 | 6/1997 |
| EP | 1 048 738 A1 | 11/2000 |
| WO | WO 00/77183 A1 | 12/2000 |

OTHER PUBLICATIONS

Sagatova et al., "Enzymatic Conversion of Phosphatidylcholine to Phosphatidylglycerol", *Applied Biochemistry and Microbiology*, vol. 32, No. 5, 1996, pp. 452–456.

Database WPI, Section Ch, Week 199146 Derwent Publications Ltd., London, GB;, AN 1988–087107 XP002192332 & JP 03 067676 B (Nippon Oils & Fats Co., Ltd.), Oct. 23, 1991. *abstract*.

* cited by examiner

*Primary Examiner*—Herbert J. Lilling
(74) *Attorney, Agent, or Firm*—Foley & Lardner

(57) ABSTRACT

The present invention provides a process for preparing a phospholipid in an aqueous system in which hydrolysis is extremely controlled, and the synthetic yield is improved.

A process for exchanging a base of a phospholipid as a raw material by subjecting the phospholipid to the action of phospholipase D in the presence of a receptor having a hydroxyl group, in which the reaction is carried out in an aqueous system, a phospholipid adsorbed on a carrier is used as a raw material phospholipid, and the receptor and the phospholipase D are used in free forms.

4 Claims, No Drawings

PROCESS FOR EXCHANGING BASES IN PHOSPHOLIPIDS

BACKGROUND OF THE INVENTION

1. Field of the Invention

The present invention relates to a process for exchanging a base in a phopholipid by subjecting a phospholipid raw material such as soybean lecithin, yolk lecithin or a synthetic phospholipid adsorbed on a carrier such as silica gel to the action of phospholipase D in an aqueous system without the use of an organic solvent in the presence of receptor having a hydroxyl group.

2. Background Art

Phospholipids are main constituents of biomembranes, and play significant roles. In addition, the phospholipids are amphiphilic materials having both polar and non-polar portions, which are natural surfactants. Because of these properties, the phospholipids are widely used as emulsifiers in the arts of foods, cosmetics and pharmaceuticals and as a base material of liposome.

Furthermore, there are reported the physiological effects in phospholipids themselves, and some phospholipids are anticipated to be applied in medical or pharmaceutical fields. It is thus considered significant in industrial fields to prepare effectively phopholipids corresponding to a variety of uses.

For instance, phosphatidylserine is also one of the natural phospholipids having these properties and has been noted recently on its physiological property as well as the other properties such as emulsification. However, while phosphatidylserine is present in bovine brain, soybean or the like, it is distributed only in small amounts in natural sources, and a variety of its synthetic methods have been investigated. Phosphatidylserine is present in a larger amount especially in brain, and its participation with energy production in brain or with neurotransmission at nerve cell membrane have been reported. Furthermore phosphatidylserine is contemplated to have physiological effects such as the alleviation of the condition of Alzheimer's patient, the inhibition of aging and the functional amelioration of brain, and it is expected as a functional foodstuff material of brain.

Phosphatidylglycerol is also an emulsifier excellent in resistance to salts and resistance to acids and thus expected to have many utilities. However, it is distributed little in nature, and thus processes for preparing it have been examined.

There has been already described the method for exchanging bases by subjecting a phospholipid to the action of phospholipase D in a system containing water as a main component (Yang, S. F. et al., J. Biol. Chem., 242, 477–484 (1967)). However, the aimed phospholipid cannot be expected to be produced in high yields in industrial scales.

Furthermore, Comfurius et al. have described the synthesis of phosphatidylserine in a yield of 45–55% with L-serine as a receptor in a bi-phase system of ethyl ether/water, and recognized the production of phosphatidic acid by hydrolysis as well (Comfurius, P., et al., Biochim. Biophys. Acta, 488, 36–42 (1977)). In this literature, after the reaction the purification of phosphatidylserine was carried out by CM cellulose column chromatography with an eluent system of chloroform/methanol. In such systems containing a large amount of water, hydrolysis also occurs and leads to the deterioration of the purity of the aimed phospholipid.

Subsequently, the reaction in the bi-phase system of organic solvents and water has been tried to be improved in many ways. Yamane et al. have described the reactions in the bi-phase systems of a variety of organic solvents (ethyl ether, ethyl acetate, benzene, and toluene) and water for controlling the production of phosphatidic acid and achieving a high synthetic yield of phosphatidylserine (90% or more) (Yamane, T. et al., Biochim. Biophys. Acta, 1003, 277–283 (1989)). Japanese Patent Laid-Open Publication No. 173092/1997 also discloses a process for preparing purified phosphatidylserine in a yield of 97% by the bi-phase system reaction with use of toluene.

In addition, Japanese Patent Publication No. 67676/1991 discloses a process for synthesizing aimed phospholipids such as phosphatidylserine or phosphatidylethanolamine by mixing and reacting a carrier having phospholipase D adsorbed thereon with a phospholipid as a raw material or a phospholipid as a raw material adsorbed on a carrier in the presence of a receptor in a system of an organic solvent containing only a small amount of water (the water content being required to be in the range of 1% or less, preferably 0.2% or less), by reason that hydrolysates are produced in reaction systems including bi-phase systems which contain a large amount of water and thus phospholipids as the aimed products cannot be obtained in effect. The aimed phospholipids, which might be synthesized effectively by the methods with use of the organic solvents, are not suitable for uses as foods.

Japanese Patent Laid-Open Publication No. 333689/2000 also discloses a process for synthesizing phosphatidylserine in an organic solvent-free aqueous system by adding calcium chloride or in addition a surfactant. However, in this method a step for incorporating these additives into the system is further required, and the water-soluble calcium chloride and surfactant will remain in the product.

The present invention is intended to solve the aforementioned problems in the prior art. That is, the object of the invention is to provide a process for exchanging a base of a phospholipid in a simple step without superfluous steps for incorporating additives into a system wherein a phospholipid as a raw material is subjected to base exchange in an aqueous system containing no organic solvent and having no superfluous additives such as water-soluble salts or surfactants incorporated thereinto, thus the product may be used for foods, hydrolysis-being controlled more effectively, the synthetic yield (or base exchange rate) of the phospholipid being improved as compared to the conventional methods with a system comprising water as the major component.

SUMMARY OF THE INVENTION

In order to achieve the aforementioned object, the process for exchanging a base in a phospholipid according to the invention comprises a process for preparing the aimed phospholipid by exchanging a base of a phospholipid as a raw material by the action of phospholipase D on the phospholipid in the presence of a receptor having a hydroxyl group, wherein the reaction is carried out in an aqueous system containing no superfluous additives such as water-soluble salts or surfactants, a phospholipid adsorbed on a carrier is used as the raw material phospholipid, and a receptor and phospholipase D are used in free states.

While the synthetic yields and purities of the aimed phospholipids obtained remain in extremely low levels in the conventional methods described above comprising water as the major component or in the method with aqueous-single phase system (both substrates and enzymes being in free states) shown below in comparative Example 1, the present invention successfully accomplishes a synthetic yield or efficiency at a high level by using a phospholipid adsorbed on a carrier as a substrate without use of superfluous additives such as water-soluble salts or surfactants. Also, while hydrolysis occurs competitively and thus the aimed phospholipid produced may also be hydrolyzed in the conventional method with a system using a large amount of water, hydrolysis reaction can be controlled and thus the purity of the product can be increased by the process of the invention. Especially, while there is described in Japanese Patent Publication No. 67676/1991 that the aimed product may be obtained only in an organic solvent containing a water content of 1% or less, hydrolysis is extremely controlled even in an aqueous system, and a phospholipid as the aimed product can be obtained efficiently in simplified steps according to the invention.

The present invention is advantageous in that a high synthetic yield or efficiency as described above can be accomplished because of the reaction in an organic solvent-free aqueous system (using a substrate adsorbed on a carrier), the aimed product thus obtained is suitable for use as foods, and the production process can be simplified.

DETAILED DESCRIPTION OF THE INVENTION

Any materials which may be used as a substrate of phospholipase D including extracts from natural products such as animal, plant and marine products, and synthetic products can be used as a raw material phospholipid in the present invention. Also, any materials including unpurified products (containing components other than the phospholipids), partially purified products or purified products may be used. The purification degree of the raw material can be appropriately determined in view of the purity of the aimed phospholipid desired. Phosphatidylcoline and phosphatidylethanolamine are particularly effective substrates as compared with the other phospholipids, and soybean lecithin and egg yolk lecithin are listed as examples of useful raw materials, which are commercially available.

Any enzymes which exhibit phosphatidyl group transferring activity can be used as the enzyme used for the invention. All of the known enzymes can be used as the phospholipase D derived from microbes, and the typical examples of the phospholipase D include those derived from Streptomyces genus such as *Streptomyces prunicolor* and *Streptomyces antibioticus,* Streptoverticillium genus such as *Streptoverticillium cinnamomeum* and *Streptoverticillium griseocarneum,* Actinomadura genus such as Actinomadura sp. Strain No. 362, Kitasatosporia genus such as *Kitasatosporia chromogema.* Phospholipase D derived from plants such as carrot, cabbage and spinach can also be used. The phospholipase D having a higher activity is preferred, but any enzymes including the commercially available ones as well as either one of crude enzymes, partially purified enzymes or purified enzymes can be used.

Any receptors can be used including choline, serine (any isomers of L-serine, D-serine, and racemic mixture may be used), alcohols such as ethanolamine, ethanol, methanol, glycerol or the like, saccharides, e.g., monosaccharides such as glucose, disaccharides such as sucrose, which receptors have a hydroxyl group and are known in the art as the receptor of such a reaction.

As the carrier having the phospholipid adsorbed thereon, any solids on which the substrates can be adsorbed may be used including silica gel, diatomaceous earth, active carbon, resins, water-insoluble calcium salts such as calcium carbonate, calcium sulfate, tricalcium phosphate, calcium monohydrogen phosphate, calcium oxalate, calcium pyrophosphate, calcium citrate, or the like. The larger the surface area, the more effective the carrier. In addition, carriers having a shape of powder, particles, blocks, sheets or the like can be selected in consideration of the procedure after reaction.

As the method for adsorbing the phospholipid on the carrier, it is preferred that when a polar solvent such as ethanol is used, the phospholipid is dissolved and brought into contact with the carrier, and then the solvent is removed by evaporation. When a non-polar solvent such as hexane is used, the phospholipid may be readily adsorbed on the carrier by dissolving the phospholipid in the solvent and contacting the carrier therewith, and the solvent may be removed by evaporation or the solvent can be removed by evaporation after filtration. In this connection, when an alcohol is used, because it may play as a receptor in the reaction, it should be removed completely. Also, adsorption may be accomplished by dispersing the phospholipid in water, adding the carrier to the dispersion, and conducting the procedures such as mixing and the like.

The process according to the invention can be carried out by suspending the carrier having the phospholipid adsorbed thereon in an aqueous solution containing a receptor and phospholipase D, and maintaining the mixture under the mild stirring. Alternately, it may be carried out in such a mode as charging the carrier having the phospholipid adsorbed thereon into a column etc., and circulating an aqueous solution containing a receptor and phospholipase D through the column.

In the process of the invention, the base exchange reaction for synthesizing the aimed phospholipid is carried out generally for 0.5–48 hours, preferably 1–24 hours.

The reaction temperature may be the optimal temperature of the enzyme, and the reaction is preferably carried out at a temperature in the range of 20–50° C.

Also, the system is preferably maintained at a pH of 4–9 during the reaction.

After the reaction has been completed, the aimed phospholipid adsorbed on the carrier can be recovered from the carrier by eluting with a solvent such as ethanol. The enzyme and the receptor may also be removed by washing with water before elution if necessary. It is also possible to reuse the reaction system in which the enzyme and the receptor still remain.

EXAMPLES

The present invention is illustrated below specifically with reference to examples and comparative examples without limitation to these examples. In this connection, percentages in the following examples refer to weight ratios in the case of Iatroscan (IATRON LABORATORIES INC.) analysis and molar ratios in the case of thin layer chromatography analysis.

Example 1

To a solution of 200 mg of yolk lecithin (purified yolk lecithin manufactured by Asahi Chemical Industry Co., Ltd., 87% phosphatidylcholine, 11% phosphatidylethanolamine, 2% others) in 30 ml of ethanol was added 1 g of silica gel (Wako Pure Chemical Industries, Ltd., Wakogel C-300), and the mixture was stirred with a stirrer. Ethanol was removed by an evaporator, and the residue was dried in a lyophilizer to give phospholipids adsorbed on silica gel.

To 81 mg of the silica gel/phospholipids prepared above were added 1.8 ml of 4.3 M aqueous L-serine solution, 0.1 ml of 1 M acetate buffer (pH 5.6), and 0.1 ml of aqueous solution of *Streptomyces antibioticus* derived phospholipase D (30.6 U/ml), and the mixture was reacted at 500 rpm at a temperature of 37° C. for 24 hours. After the reaction, a 0.1 ml portion of the reaction including silicagel was then taken out, 0.05 ml of 1 N hydrochloric acid was added, and the mixture was stirred sufficiently. 0.2 ml of chloroform/methanol (2/1) was added to and stirred with the mixture, and the chloroform layer was recovered. Analysis of the phospholipids in the chloroform layer by Iatroscan with a developing solvent of chloroform/methanol/acetic acid (40/15/6) showed a composition of 80% of phosphatidylserine, 9% of phosphatidylcholine, 9% of phosphatidic acid, and 2% of others.

Example 2

To a solution of 200 mg of soybean lecithin (SLP-PC70 manufactured by True Lecithin Kogyo K.K., 82% phosphatidylcholine, 7% phosphatidylethanolamine, 6% phosphatidic acid, 5% others) as a substrate in 30 ml of ethanol was added 1 g of silica gel (Wako Pure Chemical Industries, Ltd., Wakogel C-300), and the mixture was stirred with a stirrer. Ethanol was removed by an evaporator, and the residue was dried in a lyophilizer to give phospholipids adsorbed on silica gel.

81 mg of the silica gel/phospholipids prepared above was reacted and analyzed in the similar manner to that described in Example 1. The following analytical result was obtained; 66% of phosphatidylserine, 15% of phosphatidylcholine, 14% of phosphatidic acid, and 5% of others.

Example 3

To a solution of 200 mg of soybean lecithin (SLP-PC70 manufactured by True Lecithin Kogyo K.K., 82% phosphatidylcholine, 7% phosphatidylethanolamine, 6% phosphatidic acid, 5% others) as a substrate in 30 ml of ethanol was added 1 g of silica gel (Merck, Silica Gel 60), and the mixture was stirred with a stirrer. Ethanol was removed by an evaporator, and the residue was dried in a lyophilizer to give phospholipids adsorbed on silica gel.

81 mg of the silica gel/phospholipids prepared above was reacted and analyzed in the similar manner to that described in Example 1. The following analytical result was obtained; 80% of phosphatidylserine, 5% of phosphatidylcholine, 10% of phosphatidic acid, and 5% of others.

Example 4

To a solution of 200 mg of soybean lecithin (SLP-PC70 manufactured by True Lecithin Kogyo K.K., 82% phosphatidylcholine, 7% phosphatidylethanolamine, 6% phosphatidic acid, 5% others) as a substrate in 30 ml of ethanol was added 1 g of calcium pyrophosphate (Wako Pure Chemical Industries, Ltd.), and the mixture was stirred with a stirrer. Ethanol was removed by an evaporator, and the residue was dried in a lyophilizer to give phospholipids adsorbed on calcium pyrophosphate.

81 mg of the calcium pyrophosphate/phospholipids prepared above was reacted and analyzed in the similar manner to that described in Example 1. The following analytical result was obtained; 51% of phosphatidylserine, 33% of phosphatidylcholine, 11% of phosphatidic acid, and 5% of others.

Example 5

To a solution of 200 mg of soybean lecithin (SLP-PC70 manufactured by True Lecithin Kogyo K.K., 82% phosphatidylcholine, 7% phosphatidylethanolamine, 6% phosphatidic acid, 5% others) as a substrate in 30 ml of ethanol was added 1 g of calcium sulfate (Mutsumi Kagaku Kogyo K.K., Gypsum Dihydrate SF-CS), and the mixture was stirred with a stirrer. Ethanol was removed by an evaporator, and the residue was dried in a lyophilizer to give phospholipids adsorbed on calcium sulfate.

81 mg of the calcium sulfate/phospholipids prepared above was reacted and analyzed in the similar manner to that described in Example 1. The following analytical result was obtained; 85% of phosphatidylserine, 10% of phosphatidic acid, and 5% of others.

Example 6

To a solution of 1 g of egg yolk lecithin (Q. P. Corp.; 96% phosphatidylcholine, 4% others) in 30 ml of ethanol was added 5 g of calcium sulfate (Mutsumi Kagaku Kogyo K.K., Gypsum Dihydrate SF-CS), and the mixture was stirred with a stirrer. Ethanol was removed by an evaporator, and the residue was dried in a vacuum dry oven to give phospholipids adsorbed on calcium sulfate.

To 8.5 ml of water were added 405 mg of the calcium sulfate/phospholipids prepared above, 3 g of glycerol, 0.5 ml of 1 M acetate buffer (pH 5.6), 1 ml of an aqueous solution of phospholipase D (30 U/ml, derived from Actinomadura sp, Seikagaku Corp.), and the mixture was reacted at 200 rpm at a temperature of 30° C. for 24 hours. After the reaction, a 0.1 ml portion of the reaction including calcium sulfate was then taken out, and 0.05 ml of 1 N hydrochloric acid was added and mixed sufficiently. After 0.2 ml of chloroform/methanol (2/1) was added to the mixture and stirred, the chloroform layer was recovered. Analysis of the phospholipids in the chloroform layer by chromatographic separation with a developing solvent of chloroform/ethanol/methanol/formic acid/water (13/3/2/2/0.5), followed by coloring with Dittmer Reagent for the measurement with a chromatoscanner showed a result of a composition of 83% of phosphatidylglycerol, 9% of phosphatidylcholine, 4% of phosphatidic acid, and 4% of others.

Example 7

To a solution of 1 g of egg yolk lecithin (Q. P. Corp.; 96% phosphatidylcholine, 4% others) in 30 ml of ethanol was added 5 g of silica gel (Merck, Silica Gel 60), and the mixture was stirred with a stirrer. Ethanol was removed by an evaporator, and the residue was dried in a vacuum dry oven to give phospholipids adsorbed on silica gel.

405 mg of the silica gel/phospholipids prepared above was reacted and analyzed in the similar manner to that described in Example 6. The following analytical result was obtained; 87% of phosphatidylglycerol, 5% of phosphatidylcholine, 4% of phosphatidic acid, and 4% of others.

Example 8

To a solution of 1 g of egg yolk lecithin (Q. P. Corp.; 96% phosphatidylcholine, 4% others) in 30 ml of ethanol was added 5 g of diatomaceous earth (Showa Chemical Industry Co., Ltd., Radiolite #2000), and the mixture was stirred with a stirrer. Ethanol was removed by an evaporator, and the residue was dried in a vacuum dry oven to give phospholipids adsorbed on diatomaceous earth.

405 mg of the diatomaceous earth/phospholipids prepared above was reacted and analyzed in the similar manner to that described in Example 6. The following analytical result was obtained; 48% of phosphatidylglycerol, 41% of phosphatidylcholine, 7% of phosphatidic acid, and 4% of others.

Comparative Example 1

To a dispersion of 13.5 mg of egg yolk lecithin (purified egg yolk lecithin manufactured by Asahi Chemical Industry Co., Ltd., 87% phosphatidylcholine, 11% phosphatidylethanolamine, 2% others) in 1.8 ml of 4.3 M aqueous L-serine solution were 0.1 ml of 1 M acetate buffer (pH 5.6) and 0.1 ml of aqueous solution of *Streptomyces antibioticus* derived phospholipase D (30.6 U/ml), and the mixture was reacted at 500 rpm at a temperature of 37° C. for 24 hours. After reaction, a 0.1 ml portion of the reaction was then taken out, 0.05 ml of 1 N hydrochloric acid was added, and the mixture was stirred sufficiently. 0.2 ml of chloroform/methanol (2/1) was added to and stirred with the mixture, and the chloroform layer was recovered. Analysis of the phospholipids in the chloroform layer by Iatroscan in the similar manner to that described in Example 1 showed a composition of 6% of phosphatidylserine, 42% of phosphatidylcholine, 50% of phosphatidic acid, and 2% of others.

Comparative Example 2

To a suspension of 81 mg of the silica gel/phospholipids prepared in Example 2 and 813 mg of L-serine in 2 ml of hexane was added 0.8 mg of powder of *Streptomyces antibioticus* derived phospholipase D (corresponding to 3.06 U), and the mixture was reacted at 500 rpm at a temperature of 37° C. for 24 hours. The reaction system had a moisture content of 0.12%. After the reaction, the phospholipids were recovered and analized by Iatroscan in the similar manner to that described in Example 1. As a result, no phosphatidylserine was detected.

Comparative Example 3

To a suspension of 81 mg of the silica gel/phospholipids prepared in Example 2 and 813 mg of L-serine in 2 ml of ethyl acetate was added 1.6 mg of powder of *Streptomyces antibioticus* derived phospholipase D (corresponding to 6.12 U), and the mixture was reacted at 500 rpm at a temperature of 37° C. for 24 hours. The reaction system had a moisture content of 0.15%. After the reaction, the phospholipids were recovered and analyzed by Iatroscan in the similar manner to that described in Example 1. As a result, no phosphatidylserine was detected.

Comparative Example 4

To a dispersion of 68 mg of egg yolk lecithin (Q. P. Corp.; 96% phosphatidylcholine, 4% others) in 8.5 ml of water were added 3 g of glycerol, 0.5 ml of 1 M acetate buffer (pH 5.6) and 1 ml of an aqueous solution of phospholipase D (30 U/ml, derived from Actinomadura sp, Seikagaku Corp.), and the mixture was reacted at 200 rpm at a temperature of 30° C. for 24 hours. After the reaction a 0.1 ml portion of the reaction was then taken out, and 0.05 ml of 1 N hydrochloric acid was added and mixed sufficiently. After 0.2 ml of chloroform/methanol (2/1) was added to the mixture and stirred, the chloroform layer was recovered. The phospholipids in the chloroform layer were analyzed in the similar manner to that described in Example 6. As a result, the phospholipids had a composition of 16% of phosphatidylglycerol, 72% of phosphatidylcholine, 8% of phosphatidic acid, and 4% of others.

Comparative Example 5

To 10 ml of ethyl acetate were added 405 mg of calcium sulfate/phospholipids prepared in Example 6, 3 g of glycerol, and 11 mg of phospholipase D (30 U, derived from Actinomadura sp, Seikagaku Corp.), and the mixture was reacted at 200 rpm at a temperature of 30° C. for 24 hours. The reaction system had a moisture content of 0.19%. After the reaction was completed, the phospholipids were recovered and analyzed in the similar manner to that described in Example 6. As a result, no phosphatidylglycerol was detected.

Comparative Example 6

To 10 ml of ethyl acetate were added 405 mg of silica gel/phospholipids prepared in Example 7, 3 g of glycerol, and 11 mg of phospholipase D (30 U, derived from Actinomadura sp, Seikagaku Corp.), and the mixture was reacted at 200 rpm at a temperature of 30° C. for 24 hours. The reaction system had a moisture content of 0.17%. After the reaction was completed, the phospholipids were recovered and analyzed in the similar manner to that described in Example 6. As a result, no phosphatidylglycerol was detected.

What is claimed is:

1. A process for exchanging a base of a phospholipid as a raw material by subjecting the phospholipid to phosphate ester interchange reaction with the action of phospholipase D which is phosphodiesterase in the presence of a receptor having a hydroxyl group, in which the reaction is carried out in an organic solvent free aqueous system, a phospholipid which has been adsorbed on a carrier is used as a raw material phospholipid, and the receptor and the phospholipase D are used in free forms.

2. A process according to claim 1, wherein the receptor having a hydroxyl group is selected from the group consisting of choline, serine, alcohols and saccharides.

3. A process according to claim 1, wherein the carrier having the phospholipid adsorbed thereon is selected from the group consisting of silica gel, diatomaceous earth, active carbon, resins and water-insoluble calcium salts.

4. A process according to claim 2, wherein the carrier having the phospholipid adsorbed thereon is selected from the group consisting of silica gel, diatomaceous earth, active carbon, resins and water-insoluble calcium salts.

* * * * *